United States Patent [19]
De Bolle et al.

[11] Patent Number: 5,942,663
[45] Date of Patent: *Aug. 24, 1999

[54] BIOCIDAL PROTEINS

[75] Inventors: Miguel De Bolle, Leuven; Willem Frans Broekaert, Dilbeek; Bruno Philippe Angelo Cammue, Alsemberg, all of Belgium; Sarah Bronwen Rees, Bracknell, United Kingdom; Jozef Vanderleyden, Heverlee, Belgium

[73] Assignee: Zeneca Limited, London, United Kingdom

[ * ] Notice: This patent is subject to a terminal disclaimer.

[21] Appl. No.: 08/915,142

[22] Filed: Aug. 20, 1997

Related U.S. Application Data

[60] Continuation of application No. 08/471,329, Jun. 2, 1995, Pat. No. 5,689,048, which is a division of application No. 08/117,080, Dec. 20, 1993, Pat. No. 5,482,928.

[30]      Foreign Application Priority Data

| Mar. 11, 1991 | [GB] | United Kingdom | 9105052 |
| Mar. 19, 1991 | [GB] | United Kingdom | 9105684 |
| Mar. 10, 1992 | [WO] | WIPO | PCT/GB92/00423 |

[51] Int. Cl.$^6$ .............................. A01H 5/00; C12N 15/29; C12N 15/70; C12N 15/74; C12N 15/82
[52] U.S. Cl. ....................... 800/301; 800/279; 435/252.3; 536/23.6
[58] Field of Search .................. 435/69.1, 70.1, 435/71.1, 71.3, 172.3, 252.3, 320.1, 418, 419; 536/23.6; 800/205, 279, 301

[56]      References Cited

U.S. PATENT DOCUMENTS

| 4,701,522 | 10/1987 | Susumu | 530/370 |
| 5,340,732 | 8/1994 | Habuka | 435/193 |
| 5,482,928 | 1/1996 | DeBolle | 514/12 |

FOREIGN PATENT DOCUMENTS 375091  6/1990  European Pat. Off. .

OTHER PUBLICATIONS

Cammue et al., "Isolation and characterization of a novel class of plant . . . ", *Journal of Biological Chemistry*, vol. 267, No. 4, Feb. 1992, pp. 2228–2233.

Hubuka et al., "Expression and secretion of Mirabilis antiviral protein in Escherichia . . . ", *Journal of Biological Chemistry*, vol. 262, No. 19, Jul. 1990, pp. 10988–10992.

Watson et al., "Molecular Biology of the Gene", *The Benjamin/Cummings Publishing Company Inc.*, Menlo Park, Ca, p. 313.

*Primary Examiner*—David T. Fox
*Attorney, Agent, or Firm*—Liza D. Hohenschutz

[57]      ABSTRACT

Biocidal proteins isolated from Mirabilis have been characterized. The proteins show a wide range of antifungal activity and are active against gram-positive bacteria. DNA encoding the proteins has been isolated and incorporated into vectors. Plants transformed with this DNA have been produced. The proteins find commercial application as antifungal or antibacterial agents; transformed plants will show increased disease-resistance.

3 Claims, 11 Drawing Sheets

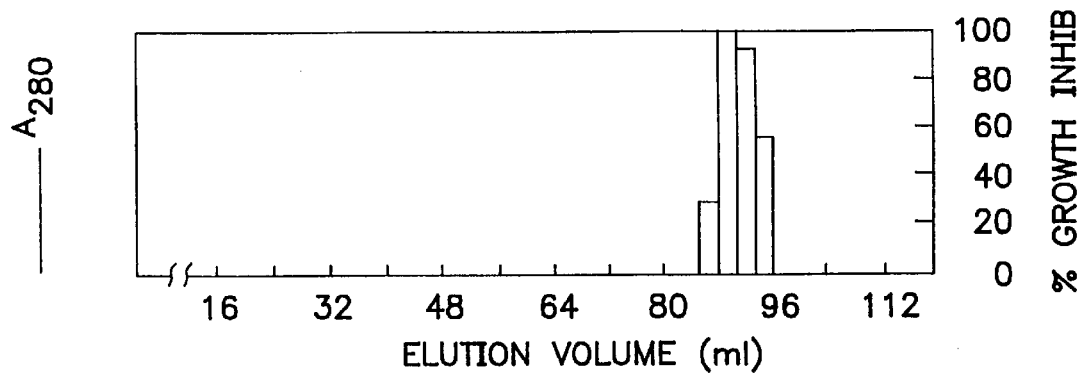
FIG. IA-I
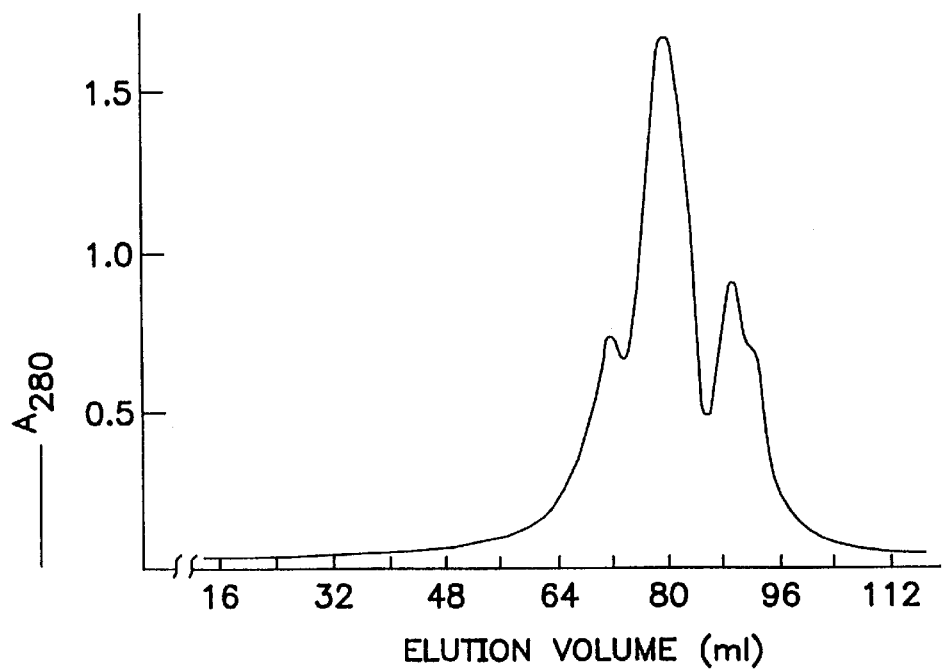
FIG. IA-2

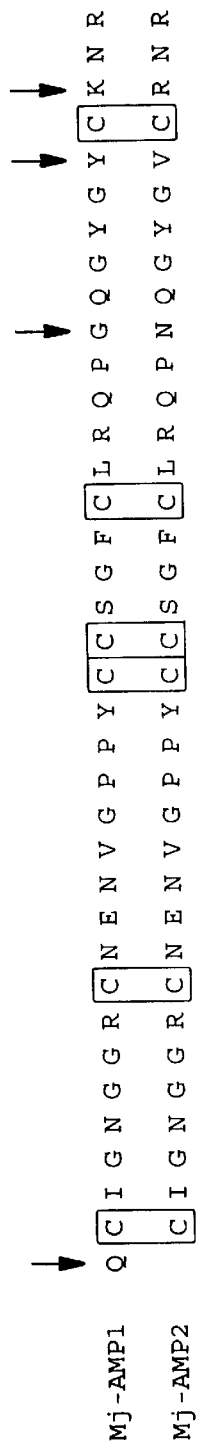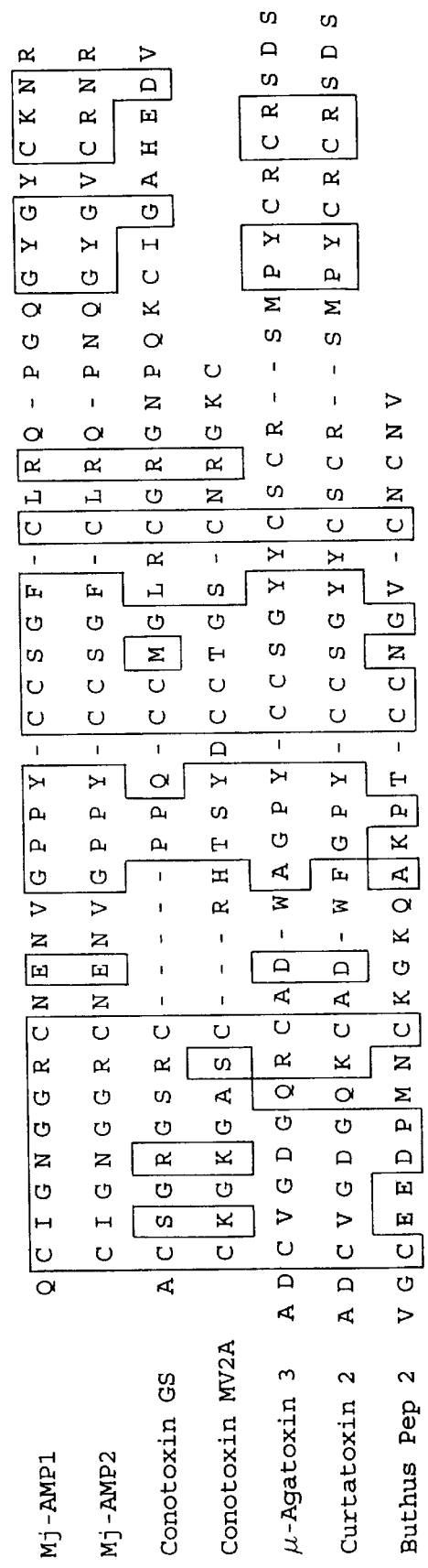

```
1    CTTCCCGTTGCCTTCCTCAAATTCGCTATTGTGTTGATTCTCTTCATT
      L  P  V  A  F  L  K  F  A  I  V  L  I  L  F  I
49   GCCATGTCCGCAATGATAGAAGCACAATGCATAGGAAATGGAGGAAGA
      A  M  S  A  M  I  E  A │Q  C  I  G  N  G  G  R
97   TGTAACGAGAACGTGGGGCCACCATACTGCTGCTCCGGTTTCTGCCTC
      C  N  E  N  V  G  P  P  Y  C  C  S  G  F  C  L
145  CGTCAACCTGGACAAGGTTATGGATATTGTAAGAACCGCTGAGCAAGA
      R  Q  P  G  Q  G  Y  G  Y  C  K  N  R│ *
193  GCATGAAAGCAAGGCCAATGTGTGGTCTACTAATTTAGCCTCAAATGT
241  TATTTATTTGCATGTCTTGTGTTTCTTAATTACCTTCTTTGTGTCTAA
289  GAAGGTATAGATCAATAGTTTCTACTTTACTACTATGAATAAGAGGCT
337  TTGATTTGGTTTAAAAAAAAAAA
```

FIG. 5

```
1    ATATCATTCAAATATACTAAACTAATTATAAAAAATGGCTAAGGTTCCA
                                                  M   A   K   V   P

50   ATTGCCTTTCTCAAATTCGTCATCGTGTTGATTCTCTTCATTGCCATG
      I   A   F   L   K   F   V   I   V   L   I   L   F   I   A   M

98   TCAGGCATGATAGAAGCATGCATAGGAAATGGAGGAAGATGTAACGAG
      S   G   M   I   E   A  | C   I   G   N   G   G   R   C   N   E

146  AACGTGGGCCCACCATACTGCTGTTCGGGTTTCTGCCTCCGTCAACCT
      N   V   G   P   P   Y   C   C   S   G   F   C   L   R   Q   P

194  AACCAAGGTTACGGTGTTTGCAGGAACCGCTAATAAGCAAAGCCCAAA
      N   Q   G   Y   G   V   C   R   N   R |  *   *

242  GTGTGGGTCACAAAATAGTAGAGTTTAGCCTCAAATGTGGTTTATATA

290  TGTAACAATCTTATATGTGTTTCTCTTGTGTTTCTTAATTACCTTCTT

338  TGTGTCTAAGAAGGTATGGATAAATAGTTTGTACTTTACTATTATGGT

386  TTTTTCTTATATCAATAAGAGGCTTTAATTAAAAAAAAAAAAAAAAAA
```

FIG. 6

BIOCIDAL PROTEINS

This is a is continuation of application Ser. No. 08/471,329, filed Jun. 2, 1995, now U.S. Pat. No. 5,689,048, which is a division of U.S. application Ser. No. 08/117,080, filed Dec. 20, 1993, now U.S. Pat. No. 5,482,928.

BACKGROUND OF THE INVENTION

This invention relates to biocidal proteins, processes for their manufacture and use, and DNA sequences coding for them. In particular, it relates to antimicrobial proteins isolated from Mirabilis.

Mirabilis comprises about 60 tropical American species, many of which are cultivated for their ornamental value as garden plants. *Mirabilis jalapa* is commonly known as "four o'clock" or "marvel of Peru", and has white, yellow or red flowers. The tuberous roots of *M jalapa* are the source of a purgative drug used as a substitute for jalap.

Although plants normally grow on substrates that are extremely rich in fungal organisms, infection remains a rare event. To keep out potential invaders, plants produce a wide array of antifungal compounds, either in a constitutive or an inducible manner. The best studied of these are phytoalexins, secondary metabolites with a broad antimicrobial activity spectrum that are specifically synthesised upon perception of appropriate defence-related signal molecules. The production of phytoalexins depends on the transcriptional activation of a series of genes encoding enzymes of the phytoalexin biosynthetic pathway. During the last decade, however, it has become increasingly clear that some plant proteins can play a more direct role in the control of phytopathogenic fungi. Several classes of proteins with antifungal properties have now been identified, including chitinases, beta-1,3-glucanases, ribosome-inactivating proteins, thionins, chitin-binding lectins and zeamatins.

Researchers at Japan Tobacco Inc have previously extracted an anti-viral protein from *Mirabilis jalapa* suspension cells (callus initially induced from leaves), and also from root and leaf tissue (Tsutomu Ikeda et al; 1987; Plant Cell Reports, 6, 216–218). This "Mirabilis anti-plant viral protein" (MAP) has a molecular weight of 24 kDa. The amino acid sequence of MAP has been determined and consists of 250 amino acids. A synthetic MAP gene of 759 base pairs has been cloned into a vector and expressed in *Escherichia coli* (Noriyuki Habuka et al; 1989; Journal of Biological Chemistry, 264 (12), 6629–6637). The following patents have been granted: J88061317 and U.S. Pat. No. 4,701,522 cover the Mirabilis MAP protein extract; J87027797 covers preparations of MAP by culturing callus. The following patent applications have also been filed: J63123386 on MAP obtained by cloning callus cells; J02186988 on preparations of the anti-viral protein by culturing *E coli* transformants; J01294694 on an anti-viral peptide (NOG-22) from Mirabilis, J01294693 on a similar synthetic peptide (NOG-53), and EP414134 on the gene encoding the anti-viral protein. In addition, Japan Tobacco have filed patent applications covering two anti-viral proteins extracted from Bougainvillea (a closely-related genus in the same family as Mirabilis): BAP-1 has a molecular weight of 33 kDa (J01272598) and BAP-2 has a molecular weight of approximately 30 kDa (J01272599).

We have now purified a new class of potent antimicrobial proteins.

SUMMARY OF THE INVENTION

According to the present invention, we provide antimicrobial proteins capable of being isolated from seeds of Mirabilis.

In further aspects, this invention comprises a vector containing a DNA sequence coding for a protein according to the invention. The DNA may be cloned or transformed into a biological system allowing expression of the encoded protein.

The invention also comprises plants transformed with recombinant DNA encoding an antimicrobial protein according to the invention.

The invention also comprises a process of combatting fungi or bacteria, whereby they are exposed to the proteins according to the invention.

A new class of potent antimicrobial proteins has been isolated from seeds of *Mirabilis jalapa*. The class includes two protein factors, hereafter called mj-AMP1 (*Mirabilis jalapa*—Antimicrobial Protein 1) and Mj-AMP2 (*Mirabilis jalapa*—Antimicrobial Protein 2) respectively. Both are dimeric proteins; Mj-AMP1 consists of two 4 kDa subunits, and Mj-AMP2 consists of two 3.5 kDa subunits. Despite their origin, their primary structure differs from all other known plant proteins and instead shows homology to insect neurotoxins found in the venom of invertebrates. The amino acid sequence of Mj-AMP1 and of Mj-AMP2 has been determined. These sequences enable manufacture of the protein using a standard peptide synthesiser.

cDNA encoding Mj-AMP1 and Mj-AMP2 has been isolated and sequenced. This DNA can be manufactured using a standard nucleic acid synthesiser, or suitable probes (derived from the known sequence) can be used to isolate the actual Mj-AMP gene(s) and control sequences from the plant genome. This genetic material can then be cloned into a biological system which allows expression of the proteins under the control of a constitutive or inducible promoter. Hence the proteins can be produced in a suitable microorganism or cultured cell, extracted and isolated for use. Suitable micro-organisms include *Escherichia coli* and Pseudomonas. Suitable cells include cultured insect cells and cultured mammalian cells. The DNA can also be transformed by known methods into any plant species, so that the antimicrobial proteins are expressed within the plant.

Plant cells according to the invention may be transformed with constructs of the invention according to a variety of known methods (Agrobacterium Ti plasmids, electroporation, microinjection, microprojectile gun, etc). The transformed cells may then in suitable cases be regenerated into whole plants in which the new nuclear material is stably incorporated into the genome. Both transformed monocot and dicot plants may be obtained in this way, although the latter are usually more easy to regenerate.

Examples of genetically modified plants according to the present invention include: fruit such as tomatoes, mangoes, peaches, apples, pears, strawberries, bananas and melons; field crops such as canola, sunflower, tobacco, sugarbeet, small-grain cereals such as wheat, barley and rice, maize and cotton: and vegetables such as carrot, lettuce, cabbage and onion.

The Mj-AMP proteins show a wide range of antifungal activity, and are also active against gram-positive bacteria. The proteins could be used as fungicides or antibiotics by application to plant parts. Their antifungal activity is salt-dependent, and may vary with the nature and concentration of the ions present in the composition. In particular, antifungal activity seems to be decreased by presence of cations. The proteins could also be used to combat fungal or bacterial disease by expression within plant bodies.

The Mj-AMP proteins can be isolated and purified from *Mirabilis jalapa* seeds, synthesised artificially from their known amino acid sequence, or produced within a suitable micro-organism by expression of recombinant DNA. The proteins may also be expressed within a transgenic plant.

BRIEF DESCRIPTION OF THE DRAWINGS

FIG. 1A shows the gel filtration chromatogram for the antimicrobial proteins and the associated graph of fungal growth inhibition.

FIG. 3A shows the complete amino acid sequences of Mj-AMP1 (SEQ ID NO:1) and Mj-AMP2 (SEQ ID NO:2); differences are indicated by arrows.

FIG. 3B shows the amino acid sequences of Mj-AMP1 and mj-AMP2, aligned with those of the neurotoxins.

FIG. 5 shows the nucleotide sequence (SEQ ID NO:11) and deduced amino acid sequence (SEQ ID NO:10) of clone MJ1 (Mj-AMP1).

FIG. 6 shows the nucleotide sequence (SEQ ID NO:13) and deduced amino acid sequence (SEQ ID NO:12) of clone MJ2 (Mj-AMP2).

DETAILED DESCRIPTION OF THE INVENTION

Figures 1, 1B:
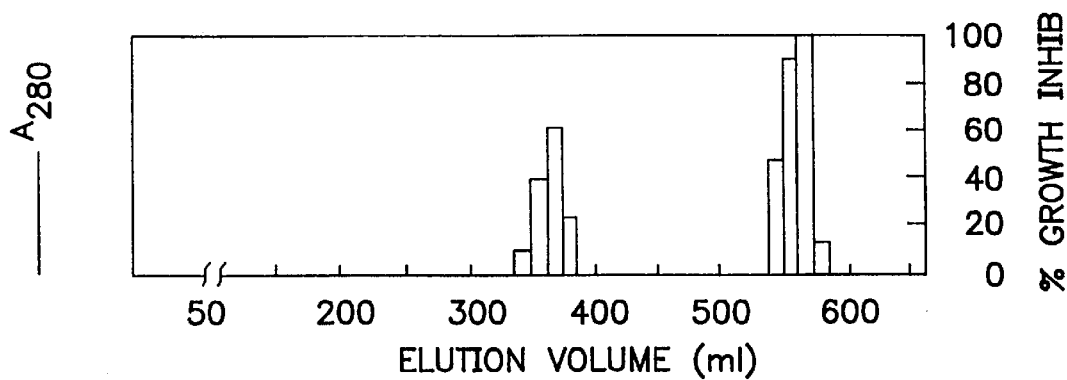
FIG. 1B shows the cation exchange chromatogram for the antimicrobial proteins and the associated graph of fungal growth inhibition.
Figures 1, 1B, 2:
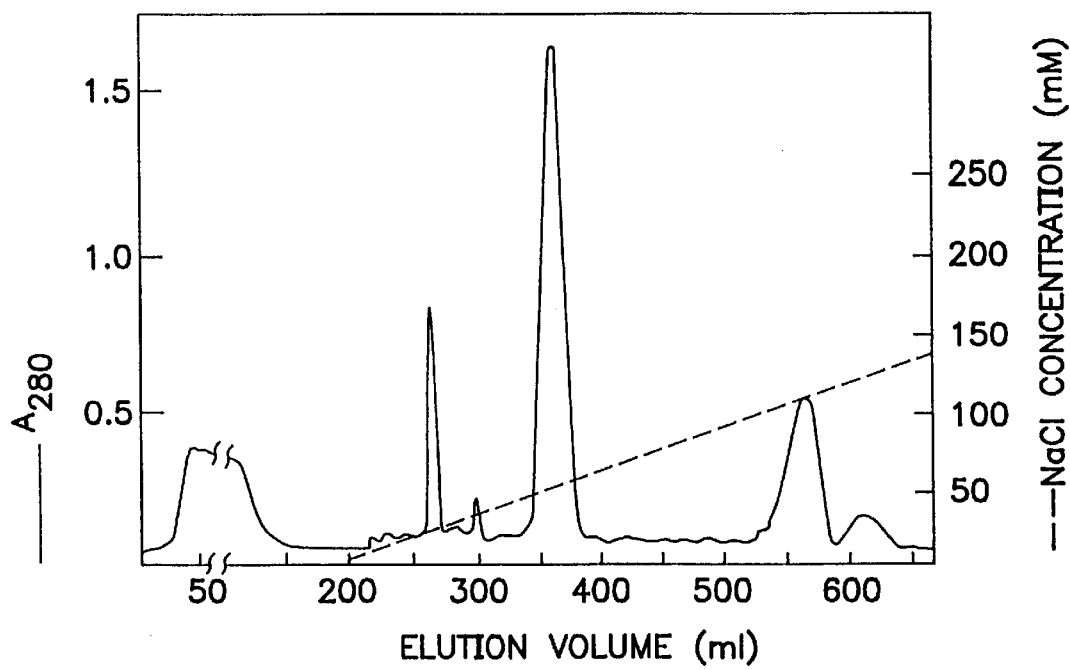

The following Examples illustrate the invention.

EXAMPLE 1

Extraction of basic heat-stable proteins from *Mirabilis jalapa* seeds

One kg of *M jalapa* seeds (purchased from Chiltern Seeds, Ulverston, Cumbria, UK) was ground in a coffee mill and the resulting meal was extracted for 2 hours at 4° C. with 2 liters of an ice-cold extraction buffer containing 10 mM $NaH_2PO_4$, 15 mM $Na_2HPO_4$, 100 mM KCl, 2 mM EDTA, 2 mM thiourea, 1 mM PMSF and 1 mg/l leupeptin. The homogenate was squeezed through cheesecloth and clarified by centrifugation (5 min at 5,000×g). Solid ammonium sulphate was added to the supernatant to obtain 35% relative saturation and the precipitate formed after standing for 1 hour at room temperature was removed by centrifugation (10 min at 5,000×g). The supernatant was adjusted to 65% relative ammonium sulphate saturation and the precipitate formed overnight at room temperature collected by centrifugation (30 min at 5,000×g). After redissolving the pellet in 300 ml 10 mm sodium phosphate buffer (pH 6) the solution was heated at 75° C. for 10 min. The coagulated insoluble material was discarded after centrifugation (20 min at 5,000×g) and the supernatant was dialyzed extensively against distilled water using benzoylated cellulose tubing (Sigma) with a molecular weight cut off of 2,000 Da. After dialysis the solution was adjusted to 50 mM Tris-HCl (pH 9) by addition of the ten-fold concentrated buffer, and subsequently passed over a Q-Sepharose Fast Flow (Pharmacia) column (12×5 cm) in equilibrium with 50 mM Tris-HCl (pH 9). The proteins in the unbound fraction were precipitated by addition of ammonium sulphate to 75% relative saturation. The precipitate was collected by centrifugation (20 min at 5,000×g) and the pellet redissolved in 15 ml phosphate buffered saline (PBS). This material represents the basic heat-stable protein fraction of *M jalapa* seeds, and was the starting material used for the isolation and purification of the *M jalapa* antimicrobial proteins.

EXAMPLE 2

Antifungal activity assay

Antifungal activity was measured by microspectrophotometry as previously described (Broekaert, WF et al; 1990; FEMS Microbiol Lett, 69, 55–60). Routinely, tests were performed with 20 μl of a (filter-sterilized) test solution and 80 μl of a fungal spore suspension ($2\times10^4$ spores/ml) in half strength Potato Dextrose Broth (Difco). Control microcultures contained 20 μl of (sterile) distilled water and 80 μl of the fungal spore suspension. Unless otherwise stated the test organism was *Fusarium culmorum* and incubation was done at 25° C. for 48 hours. Percent growth inhibition is defined as 100 times the ratio of the corrected absorbance of the control microculture minus the corrected absorbance of the test microculture over the corrected absorbance at 595 nm of the control microculture. The corrected absorbance values equal the absorbance at 595 nm of the culture measured after 48 hours minus the absorbance at 595 nm measured after 30 min. Values of growth inhibition lower than 10% are not indicated on the chromatograms.

EXAMPLE 3

Purification of antimicrobial proteins from *M jalapa* seeds

The starting material for the isolation of the *M jalapa* antimicrobial proteins was the basic heat-stable protein fraction extracted from the mature seeds. FIG. 1A illustrates how the antimicrobial proteins were purified by gel filtration chromatography. One ml fractions were applied on a Superose-12 column (50×1.6 cm) previously equilibrated with PBS. Running buffer was PBS and the flow rate 1 ml/min. The eluate was monitored for absorbance at 280 nm and collected in 2.5 ml fractions of which 2 μl was used in the microspectrophotometric antifungal activity assay described in Example 2 (results shown in the upper panel of FIG. 1A). Upon fractionation, the mixture resolved into three peaks, whereby the antifungal activity coeluted with the most retarded peak. The fractions containing antifungal activity (material from this peak) were pooled, dialyzed against 50 mM Na-MES (pH5) and subjected to cation exchange chromatography. Active fractions combined from three parallel gel filtration chromatographic runs were loaded on a S-Sepharose High Performance column (10×1.6 cm) in equilibrium with 50 mm Na-MES (pH 5). The column was eluted at 3 ml/min with a linear gradient from 0 to 150 mM NaCl in 50 mM Na-MES (pH 5), 450 ml total. The eluate was monitored for protein by measurement of the absorbance at 280 nm (results shown in the lower panel of FIG. 1B) and collected in 15 ml fractions of which 2 μl was tested in the microspectrophotometric antifungal activity assay (results shown in the upper panel of FIG. 1B). No antifungal activity was found in the unbound fraction. Application of a linear NaCl gradient allowed the separation of two factors with antifungal activity. The first factor, called Mj-AMP1 (*Mirabilis jalapa*—Antimicrobial Protein 1) eluted as a major peak around 50 mM NaCl, whereas the second factor, designated analogously as Mj-AMP2, eluted at 100 mM NaCl.

The purity of the isolated antimicrobial factors was verified by reverse-phase chromatography. HPLC profiles of the purified Mj-AMPs were obtained by loading two hundred μg amounts of Mj-AMP1 and of Mj-AMP2 on a Pep-S (porous silica $C_2/C_{18}$) column (25×0.4 cm) (Pharmacia) in equilibrium with 0.1% TFA. The column was eluted at 1 ml/min with the following gradients (solvent B is methanol containing 0.1 % TFA): 0–1 min, 0% B; 1–3 min, 0–30% B; 3–23 min, 30–80% B; 23–25 min, 80–100% B. The eluate was monitored for protein by measurement of the absorption at 280 nm. One ml fractions of the eluate were collected, freeze-dried, and finally dissolved in 100 μl distilled water of which 20 μl was used in a microspectrophotometric antifungal activity assay. Chromatography was performed on a Waters 600 HPLC station.

Figures 1, 2A:
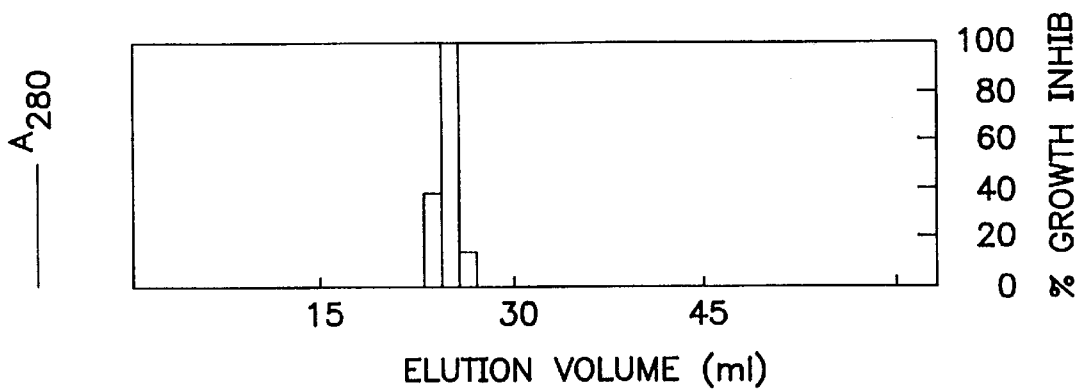
FIG. 2A shows the HPLC profile of purified mj-AMP1.
Figures 2, 2A:
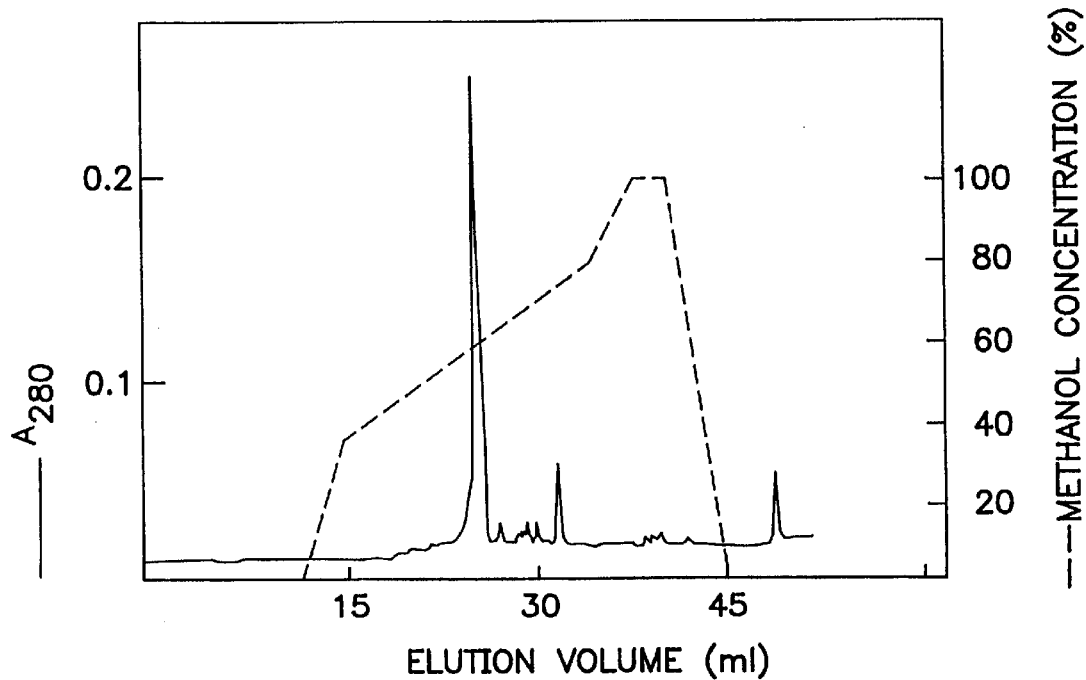
Figures 1, 2B:
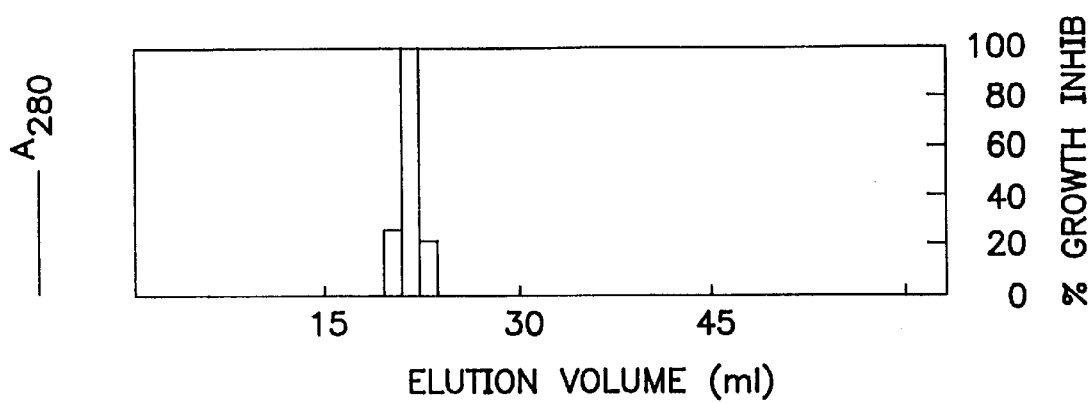
FIG. 2B shows the HPLC profile of purified Mj-AMP2.
Figures 2, 2B:
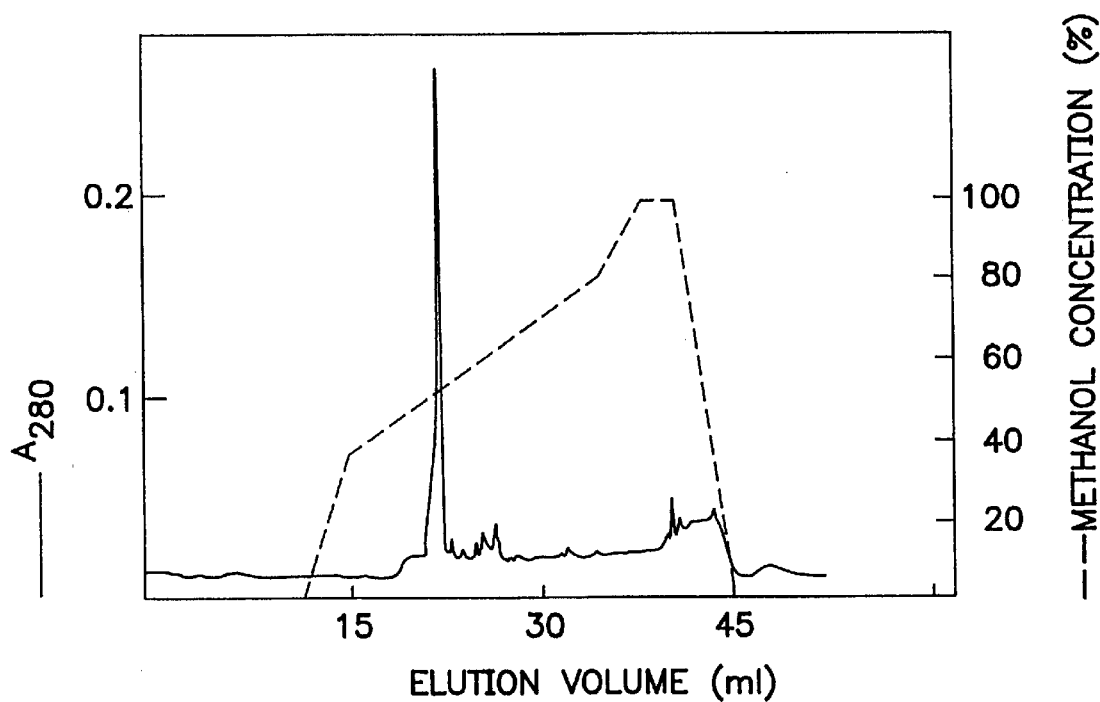
Figure 4A:
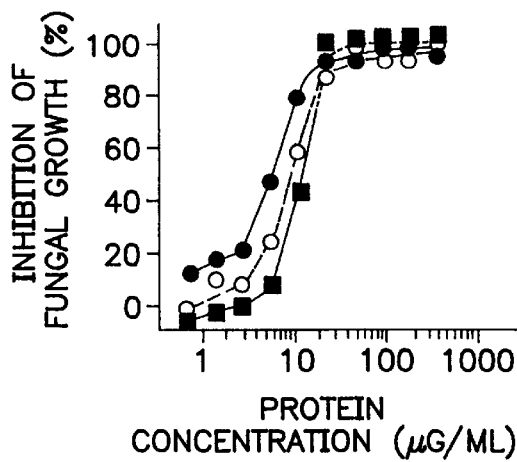
FIGS. 4A–4H show the time-dependent growth inhibition curves of fungi measured at varying concentrations of antimicrobial proteins.
Figure 4B:
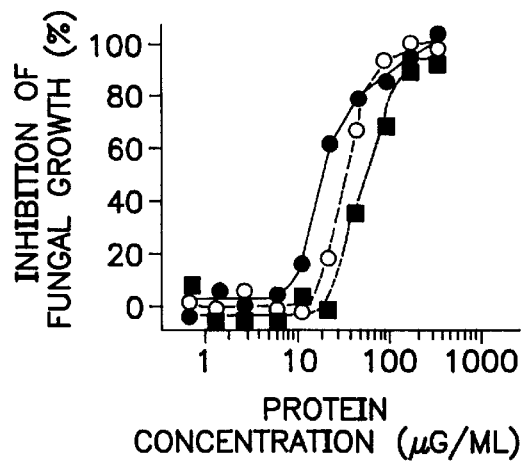
Figure 4C:
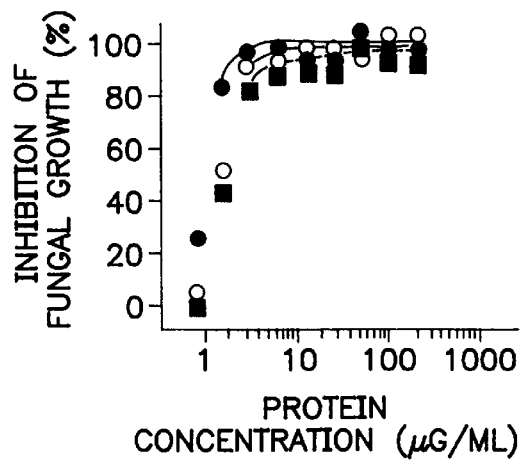
Figure 4D:
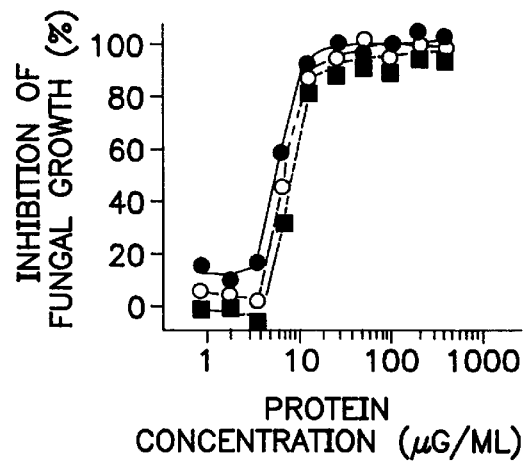
Figure 4E:
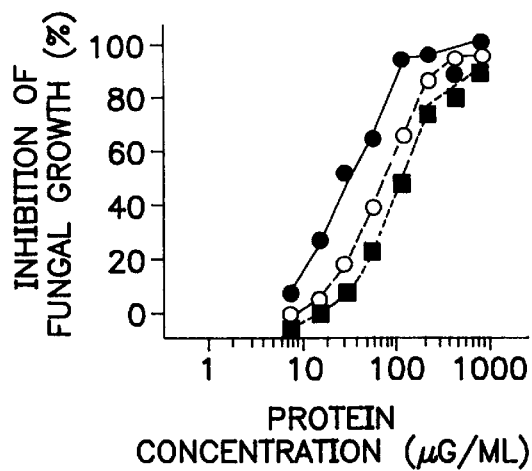
Figure 4F:
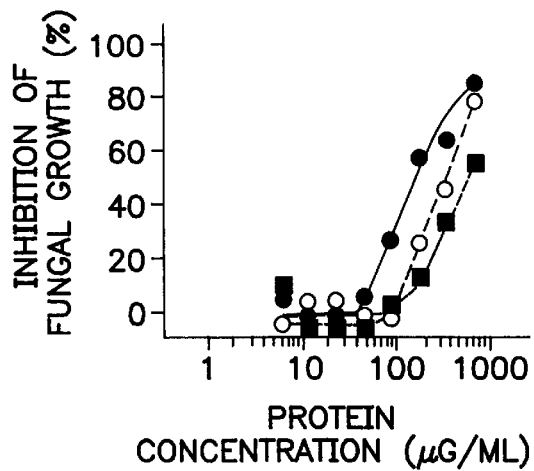
Figure 4G:
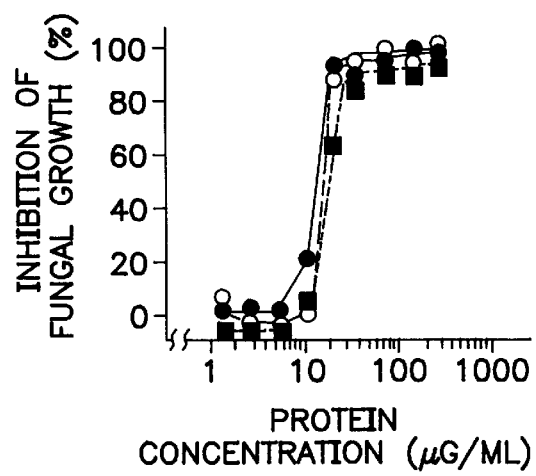
Figure 4H:
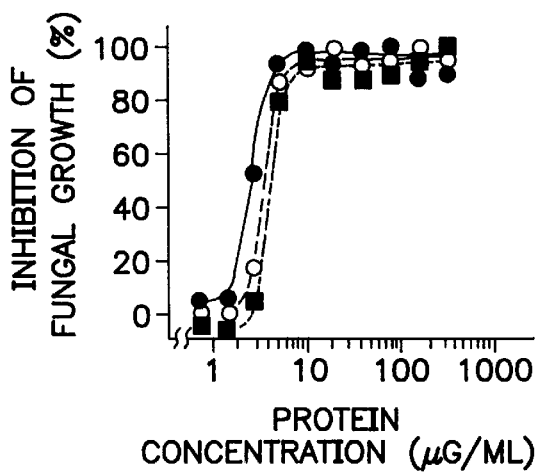

FIG. 2A and FIG. 2B show the HPLC profiles of purified Mj-AMP1 and Mj-AMP2 respectively. The lower panels show monitoring of the eluate for protein by measurement of the absorption at 280 nm. Results of the microspectrophotometric antifungal activity assay are shown in the upper panels. Both Mj-AMP1 and Mj-AMP2 yielded single, well resolved, major peaks that coeluted exactly with the antifungal activity.

EXAMPLE 4

Molecular structure of the purified antimicrobial proteins

The molecular structure of the Mj-AMPs was further analysed. Electrophoresis was performed on precast commercial gels (PhastGel High Density from Pharmacia) using a PhastSystem (Pharmacia) electrophoresis apparatus. The sample buffer contained 200 mM Tris-HCl (pH 8.3), 1% (w/v) SDS, 1 mM EDTA, 0.005% bromophenol blue and, unless otherwise stated, 1% (w/v) dithiothreitol (DTT). Silver staining of proteins in the gel was done according to Development Technique File no 210 of PhastSystem (Pharmacia LKB Biotechnology, Uppsala, Sweden), and diffusion blotting followed by silver staining of the blots was performed as described in Development Technique File no 222 of PhastSystem.

Sodium dodecyl sulphate polyacrylamide gel electrophoresis (SDS-PAGE) of the unreduced mj-AMPs failed to reveal the presence of proteins. However, when nitrocellulose blots were prepared from the gels, Mj-AMP1 and Mj-AMP2 appeared on the blots as single bands with molecular weights of 8 kDa and 7 kDa, respectively. Unreduced protein samples (200 ng) were dissolved in sample buffer without DTT, separated on PhastGel High Density (Pharmacia), blotted on to nitrocellulose and silver-stained on the blot. Myoglobin fragments were used as molecular weight markers. The reduced Mj-AMPs could be stained directly in the gel upon SDS-PAGE, showing rather diffuse bands in the apparent molecular weight zone of 3 to 4 kDa. Protein samples (200 ng) were reduced in sample buffer containing DTT, separated on PhastGel High Density and silver-stained in the gel.

It appears therefore that the antimicrobial factors are dimeric proteins stabilised by disulphide bridges, each comprised of two identical subunits (about 4 kDa and 3.5 kDa for Mj-AMP1 and Mj-AMP2, respectively). Attempts to determine the molecular weight of the native Mj-AMPs by gel filtration on either Superose-12 or Superdex yielded clearly underestimated values (between 1 and 2 kDa), most probably due to interactions with the gel matrices.

Periodic Acid Schiff's (PAS) staining of reduced Mj-AMPS separated by SDS-PAGE was negative, suggesting that their polypeptides are non-glycosylated. PAS staining for glycoproteins was done by the method of Zacharius, RM et al (1969; Anal Biochem, 30, 148–152) using ovalbumin (3.2% carbohydrate) as a positive control sample. The pI values of Mj-AMP1 and Mj-AMP2 were determined by isoelectric focusing and found to be about 10.5 for both proteins. Isoelectric focussing was done on precast Immobiline Dry Strips (Pharmacia) using marker proteins in the pI range from 4.7 to 10.6 (Pharmacia).

All cysteine residues of mj-AMP2 appeared to participate in disulphide bonds, as unreduced Mj-AMP2 did not contain free thiol groups. Likewise, Mj-AMP1 only reacted with thiol reagents in its reduced but not in its unreduced state. Thiol group determination was done by the dithionitrobenzoic acid method of Ellman, GL (1959; Arch Biochem Biophys, 82, 70–74) using 10 nmol of protein. Reduced protein samples were prepared by reaction with 10 mM DTT for 1 hour at 45° C. followed by extensive dialysis against distilled water using benzoylated cellulose tubing (Sigma) with a molecular weight cut off of 2 kDa.

EXAMPLE 5

Amino acid sequencing of the MJ-AMPs

Cysteine residues of antimicrobial proteins were modified by S-carboxyamidomethylation as follows: 100 μg amounts of purified proteins were dissolved in 150 μl 0.3 M Tris-HCl (pH 8.6) containing 30 mM DTT and reacted for 1 hour at 45° C. iodoacetamide was added to a final concentration of 100 mN and the mixture was kept in the dark at 37° C. for 1 hour. The reaction was finally quenched by addition of DTT to a final concentration of 100 mM and allowed to react for an additional hour at 37° C. Desalting was done by High Performance Liquid Chromatography (HPLC) on a Pep-S (porous silica $C_2/C_{18}$) (Pharmacia) column (25×0.4 cm). The carboxyamidomethylated proteins were recovered by eluting the column with a linear gradient from 0.1% trifluoroacetic acid (TFA) to 2-propanol containing 0.1% TFA. The resulting protein fractions were subjected to amino acid sequence analysis in a 477A Protein Sequencer (Applied Biosystems) with on-line detection of phenylthiohydantoin amino acid derivatives in a 120A Analyser (Applied Biosystems).

Sequence data were obtained for 37 residues of Mj-AMP1, after treatment with pyroglutamate amino peptidase (to remove a blocked N-terminal residue) and with trypsin (to generate internal peptides). The molecular mass of Mj-AMP1 was verified by fast atom bombardment mass spectroscopy and found to be 3976 daltons, corresponding exactly to the predicted molecular mass. The sequence was homologous with Mj-AMP2, featuring differences at amino acid 28 (an asparagine replaced by a glycine), amino acid 33 (a valine replaced by a tyrosine), and amino acid 35 (an arginine replaced by a lysine). A glutamine at amino acid 1 was further identified in Mj-AMP1. Both peptides contain 6 cysteine residues. FIG. 3A shows the complete amino acid sequences of Mj-AMP1 and Mj-AMP2; differences are indicated by arrows.

The Mj-AMP sequences were found to be homologous to neurotoxins found in the venom of invertebrates including μ-agatoxins from the spider *Agelenopsis aperta* (Skinner, WS et al; 1989; J Biol Chem, 264, 2150–2155), conotoxins from marine snail Conus sp. (Olivera, BM, et al; 1985, Science, 230, 1338–1343), toxins from the Buthotus scorpion (Fazal A et al, 1989, FEBS Letters 257 260–2), and curtatoxins (Stapleton et al, 1990, J Biol Chem, 265(4), 2054–2059). FIG. 3B shows the amino acid sequences of Mj-AMP1 and Mj-AMP2, aligned with those of the neurotoxins. Homologous amino acids are boxed. Dashes indicate gaps introduced for optimal alignment of the sequences.

EXAMPLE 6

Stability of the antifungal activity of the Mj-AMPs

Table 1 summarises the results of further testing of the stability of the antifungal activity of the Mj-AMPs. Tests for antifungal activity were performed with 20 µl samples diluted five-fold with growth medium containing *Fusarium culmorum* spores ($2\times10^4$ spores/ml), according to the assay method given in Example 2. Control samples contained either Mj-AMP1 at 500 µg/ml or Mj-AMP2 at 100 µg/ml in 10 mM sodium phosphate buffer (pH 7). Reduction was done by addition of DTT at 2.5 mM followed by incubation at 37° C. for 2 hours. pH stability was tested in the following buffers: 20 mM glycine-HCl (pH 2 and 3); 20 mM diethanolamine-HCl (pH 10); and 20 mM glycine-NaOH (pH 11). After 1 hour of incubation in the appropriate buffers the samples were dialyzed for 16 hours against 10 mm sodium phosphate buffer (pH 7). For digestions, proteases were added at 100 µg/ml and incubated at 37° C. for 16 hours.

TABLE 1

Stability of the antifungal activity of Mj-AMPs

| Treatment | Relative antifungal activity (shown as % of control activity) | |
|---|---|---|
| | Mj-AMF1 | Mj-AMP2 |
| Control | 100 | 100 |
| Reduction | <6 | <3 |
| 80° C., 10 min | 100 | 100 |
| 90° C., 10 min | 100 | 100 |
| 100° C., 10 min | 100 | 100 |
| pH 2, 60 min | 100 | 100 |
| pH 3, 60 min | 100 | 100 |
| pH 10, 60 min | 100 | 100 |
| pH 11, 60 min | 100 | 100 |
| Pronase E digestion | 50 | 25 |
| Chymotrypsin digestion | 12 | 50 |
| Trypsin digestion | 75 | 100 |
| Proteinase K digestion | 100 | 100 |

After reduction of their disulphide bonds, Mj-AMPs completely lost their antifungal activity against *F culmorum*. The activity of the native proteins, however, was not affected by heat treatments at up to 100° C. for 10 minutes, and was stable over the pH range of 2 to 11. Mj-AMP1 was sensitive to the protease chymotrypsin, but resisted almost completely digestion by pronase E, trypsin and proteinase K, whereas Mj-AMP2 was most sensitive to pronase E treatment.

EXAMPLE 7

Antifungal potency of the Mj-AMPs

The antifungal potency of the Mj-AMPs was examined on 13 different plant pathogenic fungi, and compared to that of two known antifungal proteins, *Urtica dioica* agglutinin or UDA (Broekaert, WF et al; 1989; Science, 245, 1100–1102) and β-purothionin (Hernandez-Lucas, C et al; 1974; Appl Microbiol, 28, 165–168). Fungi were grown on six cereal agar under white fluorescent light and spores were harvested and stored as previously described (Broekaert, WF et al; 1990; FEMS Microbiol Lett, 69, 55–60). The following fungal strains were used: *Alternaria brassicola* MUCL 20297, *Ascochyta pisi* MUCL 30164, *Botrytis cinerea* MUCL 30158, *Colletotrichum lindemuthianum* MUCL 9577, *Fusarium culmorum* IMI 180420, *Fusarium oxysporum* f.sp. pisi IMI 236441, *Fusarium oxysporum* f.sp. lycopersici MUCL 909, *Nectria haematococca* Collection Van Etten 160-2-2, *Phoma betae* MUCL 9916, *Pyrenophora tritici-repentis* MUCL 30217, *Pyricularia oryzae* MUCL 30166, *Venturia inaegualis* MUCL 15927, *Verticillium dahliae* MUCL 19210. UDA was isolated from stinging nettle (Urtica dioica) rhizomes as previously described (Peumans, WJ et al; 1983; FEBS Lett, 177, 99–103). The β-purothionin was purified from wheat endosperm by the method of Redman, DG and Fisher, N (1969; J Sci Fd Agric, 20, 427–432).

Table 2 summarises the results. Serial dilutions of Mj-AMP1, Mj-AMP2, UDA and β-purothionin were applied to fungi and the percent growth inhibition measured by microspectrophotometry (as described in Example 2). The concentration required for 50% growth inhibition after 48 hours of incubation was taken as the $IC_{50}$ value, which was calculated from the dose-response curves. The $IC_{50}$ of the slow growing fungus *Venturia inaequalis* was measured after 10 days of incubation.

The concentrations required for 50% inhibition of fungal growth after 48 hours of incubation ($IC_{50}$) varied from 6 to 300 µg/ml for Mj-AMP1, from 0.5 to 20 µg/ml for Mj-AMP2, from 0.5 to 15 µg/ml for β-purothionin, and from 20 to over 1,000 µg/ml for UDA depending on the test organism. On an average basis the obtained antifungal activity series is as follows: Mj-AMP2=β-purothionin>Mj-AMP1>UDA. Some fungi, such as *B cinerea, C lindemuthianum* and *V inaequalis*, are clearly more sensitive to Mj-AMP2 than to β-purothionin. Conversely, the latter protein is most effective in deterring growth of other fungi such as *F oxysporum* f.sp. pisi and *P tritici-repentis*.

With all tested antifungal proteins, the extent of growth inhibition tended to decrease as the incubation time increased. For instance, the $IC_{50}$ value of Mj-AMP1 on *C lindemuthianum* rose from 6 µg/ml after 48 hours of incubation to 12 µg/ml after 72 hours. The time-dependent drop in antifungal activity, however, was less pronounced for Mj-AMP2 and β-purothionin than for Mj-AMP1 or UDA. Also, Mj-AMP2 and β-purothionin characteristically produced steeper dose-response curves than Mj-AMP1 or UDA. FIG. 4 shows the time-dependent growth inhibition curves of the fungi *Colletotrichum lindemuthianum* (panels A, C, E, G) and *Alternaria brassicola* (panels B, D, F, H) measured at varying concentrations of the following proteins: Mj-AMP1 (panels A and B), Mj-AMP2 (panels C and D), UDA (panels E and F), and β-purothionin (panels G and H). The percent growth inhibition was recorded after 48 h (● . . . ●), after 60 h (0 . . . 0) or after 72 h (■ . . . ■).

TABLE 2

Antifungal activity of MJ-AMPS and other antifungal proteins on different phytopathogenic fungi

| | | IC$_{50}$ (μg/ml) | | | |
|---|---|---|---|---|---|
| Fungus | | Mj-ANP1 | Mj-AMP2 | UDA | β-puro-thionin |
| A | brassicola | 20 | 6 | 200 | 3 |
| A | pisi | 200 | 6 | 1,000 | 3 |
| B | cinerea | 60 | 2 | >1,000 | 12 |
| C | lindemuthianum | 6 | 1 | 20 | 15 |
| F | culmorum | 30 | 3 | >1,000 | 1 |
| F | oxysporum f.sp. pisi | 15 | 5 | >1,000 | 0.5 |
| F | oxysporum f.sp. lycopersici | 200 | 10 | *ND | ND |
| N | haematococca | 15 | 0.5 | 200 | 1 |
| P | betae | 25 | 6 | 50 | 4 |
| P | tritici-repentis | 300 | 20 | 200 | 4 |
| P | oryzae | 6 | 0.5 | ND | ND |
| V | dahliae | 12 | 0.5 | 80 | 0.5 |
| V | inaequalis | 12 | 1 | 1,000 | 5 |

* ND = not determined

EXAMPLE 8

Antifungal activity of the Mj-AMPs against foliar diseases: in vivo test

The basic heat-stable protein fraction from *Mirabilis jalapa* and a pure sample of Mj-AMP1 were tested against foliar fungal diseases of plants using the following technique.

The plants were grown in John Innes Potting Compost (No 1 or 2) in 4 cm diameter mini-pots. The protein preparation was formulated immediately prior to use by dissolving in sterile deionised water and diluting to the appropriate concentration. It is assumed that the protein extract contains approximately 1% active ingredient. A pure sample of Mj-AMP1 was similarly prepared. The formulations were applied to the plants as a foliar spray. The spray was applied to maximum discrete droplet retention. Tween 20, to give a final concentration of 0.05%, was added when the spray was applied to cereals. The protein preparation was applied to the foliage (by spraying) one or two days before the plant was inoculated with the disease (protectant application). Foliar pathogens were applied by spray as spore suspensions on to the leaves of test plants. After inoculation, the plants were put into an appropriate environment to allow infection to proceed and then incubated until the disease was ready for assessment. The period between inoculation and assessment varied from four to fourteen days according to the disease and environment.

Results are shown in Table 3 for the three fungal pathogens: *Septoria nodorum* (Fungi Imperfecti) tested on wheat, *Plasmopara viticola* (Phycomycete) tested on grapevine, and *Cercospora beticola* tested on sugarbeet. The disease control was recorded by the following grading: 4=no disease; 3=trace–5% of disease on untreated plants; 2=6–25% of disease on untreated plants; 1=26–60% of disease on untreated plants; 0=61–100% of disease on untreated plants.

TABLE 3

Control of fungal diseases invivo by Mirabilis proteins

| | FOLIAR SPRAY CONC. CRUDE PROTEIN EXTRACT | | | Mj-AMP1 100 μg/ml |
|---|---|---|---|---|
| TEST ORGANISM | 10 mg/ml | 2.5 mg/ml | Untreated | control |
| S nodorum | 2–3 | 0 | 0 | — |
| P viticola | 4 | 4 | 0 | — |
| C beticola | — | — | 0 | 3 |

These results confirm that the Mirabilis protein extract or the purified Mj-AMP1 peptide can act as a fungicide in vivo when applied as a foliar spray.

EXAMPLE 9

Antifungal activity of the Mj-AMPs against foliar diseases: in vitro test

The protein preparation as defined in Example 8 was also tested for activity against a spectrum of fungal pathogens in vitro. A measured aliquot of the formulated material was dispersed in an agar medium (Petris minimal medium, consisting of a salts solution of 2 g Ca(NO$_3$)$_2$, 0.725 g MgSO$_4$, 0.725 g KH$_2$PO$_4$, 0.6 g KCl, 17.2 g NaH$_2$PO$_4$, 17.725 g Na$_2$HPO$_4$ in 1000 ml of water, plus an agar solution consisting of 10 g Technical Agar no 3 (Oxoid) and 50 g sucrose in 800 ml water). The agar was subsequently inoculated with a range of pathogens using either spore suspensions or mycelial plugs. The agar plates were then inoculated for a period of up to 5 days before assessment.

Results are shown in Table 4. The disease control was recorded by the following grading: 4=no growth of pathogen (complete inhibition); 3=trace growth of pathogen; 2=restricted/moderate growth of pathogen; 0=no inhibition of pathogen; M=missing result.

TABLE 4

Control of fungal diseases invitro by Mirabilis protein extract

| | CONCENTRATION OF CRUDE PROTEIN EXTRACT | | Untreated |
|---|---|---|---|
| TEST ORGANISM | 10 mg/ml | 2.5 mg/ml | control |
| Penicillium pinophilum | 4 | 2 | 0 |
| Aureobasidium pullulans | 4 | 2 | 0 |
| Aspergillus niger | 2 | 3 | 0 |
| Penicillium digitatum | 4 | 4 | 0 |
| Colletotrichum musae | 2 | 2 | 0 |
| Botrytis cinerea | 4 | 3 | 0 |
| Fusarium culmorum | 4 | 4 | 0 |
| Geotrichium candidum | 4 | 3 | 0 |
| Verticillium albo-atrum | M | 2 | 0 |

The protein extract shows a broad spectrum of antifungal activity at both rates tested.

EXAMPLE 10

Inhibitory activity of Mj-AMPs against yeast

The inhibitory activity of Mj-AMPs against yeast, *Saccharomyces cerevisiae* was tested. The results shown in Table 5 indicate that Mj-AMPs do inhibit the growth of yeast at concentrations of 500 μg/ml or above.

TABLE 5

Inhibitory activity of purified Mj-AMPS

| | CONCENTRATION ($\mu$g/ml) | | | | | |
|---|---|---|---|---|---|---|
| | without Ca/K | | | with Ca/K | | |
| | 500 | 50 | 5 | 500 | 50 | 5 |
| Mj-AMP1 | +++ | +++ | + | +++ | − | − |
| Mj-AMP2 | +++ | +++ | +++ | +++ | +++ | − |

+++:complete inhibition
+:some inhibition
−:no inhibition

EXAMPLE 11

Antibacterial activity of the Mj-AMPs: in vitro test

The antibacterial activity of the Mj-AMPs was tested against a range of gram-positive and gram-negative bacteria: *Bacillus megaterium, Sarcina lutea, Escherichia coli* and *Erwinia carotovora*. β-purothionin and UDA were also tested for comparison (see Example 7). Tests were performed in soft agarose medium containing 1% tryptone and, with or without 1 mM $CaCl_2$ and 50 mM KCl. Absorbance, 595 nm, of the culture was measured after 48 hours. Results are shown in Table 6.

TABLE 6

Antibacterial activity of Mj-AMPS, β-purothionin and UDA

| | $IC_{50}$ ($\mu$g/ml) | | | |
|---|---|---|---|---|
| Bacterium | Mj-AMP1 | Mj-AMP2 | β-pt | UDA |
| MEDIUM −Ca/K | | | | |
| B megaterium | 6 | 2 | 1 | 250 |
| S lutea | 100 | 50 | 8 | >500 |
| E coli | >500 | >500 | 200 | >500 |
| E carotovora | >500 | >500 | >500 | >500 |
| MEDIUM +Ca/K | | | | |
| B megaterium | 20 | 10 | 1 | >500 |
| S lutea | >500 | >500 | 20 | >500 |
| E coli | >500 | >500 | >500 | >500 |
| E carotovora | >500 | >500 | >500 | >500 |

The results show that while the Mj-AMPs appear to have no activity against gram-negative bacteria, they do inhibit growth of gram-positive bacteria.

EXAMPLE 12

Molecular cloning and sequence of the Mj-AMP cDNAs

Fully matured seeds of *mirabilis jalapa* were collected from outdoor grown plants, immediately frozen in liquid nitrogen and stored at −80° C. Total RNA was extracted from 15 g of pulverised seeds by the method of De Vries et al (1988, Plant Molecular Biology Manual, B6, 1–13). Poly (A)+ RNA was purified by oligo (dT)-cellulose affinity chromatography as described by Silflow et al (1979, Biochemistry, 18, 2725–2731) yielding about 10 g of poly (A)+ RNA. Double-stranded cDNAs were prepared from 2 g of poly (A)+ RNA according to Gubler and Hoffman (1983, Gene, 25, 263–269) using the cDNA Synthesis System Plus of Amersham. The cDNAs were cloned into the λgt10 phage vector (Amersham) after ligation to EcoRI linkers (Amersham) according to the manufacturer's instructions. Phage DNA was packaged in vitro with the Gigapack II Gold packaging system (Stratagene).

A DNA probe for screening of the cDNA library was produced by polymerase chain reaction (PCR) as follows. Two degenerate oligonucleotides were synthesised: OWB3 (5'TGYATHGGNAAYGGNGGNMGNTG) and OWB4 (5'ACNCCRTANCCYTGRTTNGGYTG). OWB3 corresponds to amino acids 1 to 8 of Mj-AMP2 and has a sense orientation. OWB4 corresponds to amino acids 25 to 32 of Mj-AMP2 and has an antisense orientation. PCR was performed with the Taq polymerase under standard conditions (Sambrook et al, 1989, Molecular Cloning, Cold Spring Harbour Lab Press) using OWB3 and OWB4 as amplimers and 25 ng of cDNA as target DNA. The temperature programme included an initial step at 94° C. for 5 min. 30 cycles (94° C. for 1 min; 45° C. for 2 min; 72° C. for 3 min) and a final step at 72° C. for 10 min. The 100 bp PCR amplification product was purified on a 3% agarose (NuSieve, FMC) gel and reamplified by PCR under the same conditions except that the reaction mixtures contained 130 $\mu$M dTTP and 70 $\mu$M digoxigenin-11-dUTP instead of 200 $\mu$M dTTP. The digoxigenin-labelled PCR product was purified on a 3% NuSieve agarose gel.

About 100,000 plaque forming units of the λgt10 cDNA library were screened with the digoxigenin-labelled PCR product by in situ plaque hybridisation using nylon membranes (Hybond -N, Amersham). Membranes were air-dried and DNA was crosslinked on the membranes under UV light (0.15 $J/cm^2$). Hybridisation was performed for 16 hours at 68° C. in 5×SSC, 1% blocking reagent (Boehringer Mannheim), 0.1% N-lauroylsarcosine, 0.02% sodium dodecylsulphate containing 10 ng/ml of heat denatured digoxigenin-labelled probe. Non-specifically bound probe was removed by rinsing twice for 5 min in 2×SSC/0.1% SDS at 25° C. and twice for 15 min in 0.1×SSC/0.1% SDS at 68° C. Detection of the probe was done using anti-digoxigenin antibodies linked to alkaline phosphatase (Boehringer Mannheim) and its substrate 5-bromo-4-chloro-3-indolyl phosphate (Boehringer Mannheim) according to the manufacturer's instructions. Positive plaques were purified by two additional screening rounds with the same probe under the same conditions. Inserts from purified plaques were subcloned into the EcoRI site of pEMBL18 (Dente et al, 1983, Nucl Acid Res, 11, 1145–1155). Nucleotide sequencing was done with an ALF automated sequencer (Pharmacia) using fluoresceine-labelled M13 forward and reverse primers (Pharmacia). Sequence analysis was performed by the PC-gene software (Intelligenetics).

Inserts from two positive clones, MJ1 and MJ2 were subjected to nucleotide sequence analysis.

MJ1 is 360 nucleotides in length and appears to be truncated at its 5' end. The coding region contains 61 amino acids including the 37 amino acids of Mj-AMP1 at the carboxy-terminal part. Again, the amino-terminal part (24 amino acids) has all the features of a signal peptide but is truncated since it lacks an initial methionine. The 3' untranslated region is 172 nucleotides long and includes a putative polyadenylation signal (AATAAG) at position 326 and a 12-nucleotide poly (A) tail.

MJ2 is 433 nucleotides long and contains an open reading frame of 63 amino acids. The 36 carboxy-terminal amino acids correspond exactly to the amino acid sequence of Mj-AMP2, whereas the 27 amino-terminal amino acids have a predicted signal peptide structure obeying the (−1, −3)-rule (von Heijne, 1985, Mol Biol, 184, 99–105). MJ2 has 34-nucleotide and 210-nucleotide untranslated regions at the 5' and 3' end, respectively. A putative polyadenylation signal (AATAAG) is located at position 399 and is followed 11 nucleotides downstream by an 18-nucleotide poly (A) tail.

FIGS. 5 and 6 show the nucleotide sequences and deduced amino acid sequences of clones MJ1 and MJ2, respectively. The open boxes correspond to the amino acid sequence of the mature Mj-AMPs. Stop codons are marked with asterisks and the potential polyadenylation sites are underlined.

EXAMPLE 13

Construction of the expression vector pMDB1

Figure 7:
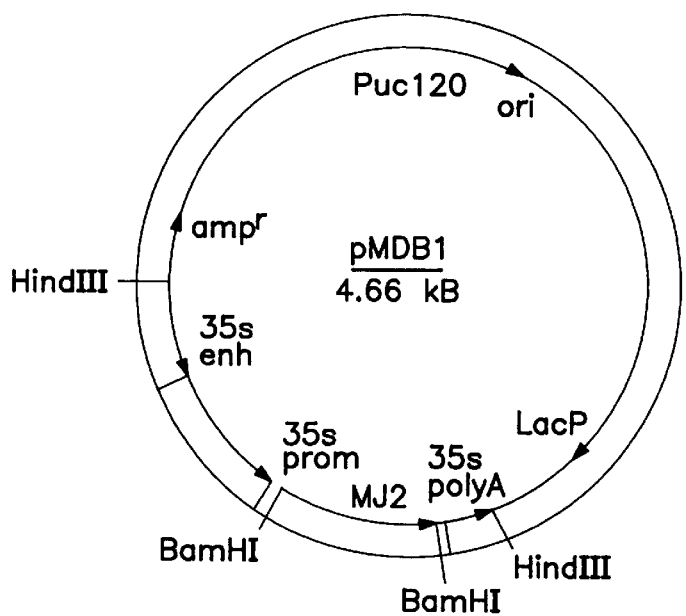
FIG. 7 shows the construction of the expression vector pMDB1.

The insert MJ2 (containing the Mj-AMP2 sequence) was removed by BamHI digestion from the pEMBL18+ vector and sub-cloned in a BamHI site of the expression vector pFAJ3002. pFAJ3002 is a modification of the expression vector pFF19 (Zimmermans et al, 1990, J Biotechnology, 14, 333–344) comprising a HindIII substitution of an EcoRI site and a CaMV35S double enhancer sequence. A clone comprising MJ2 in a sense orientation was designated pMDB1: its construction is shown in FIG. 7.

EXAMPLE 14

Construction of the plant transformation vector pMDB2 for extracellular expression of Mj-AMP2

Figure 8:
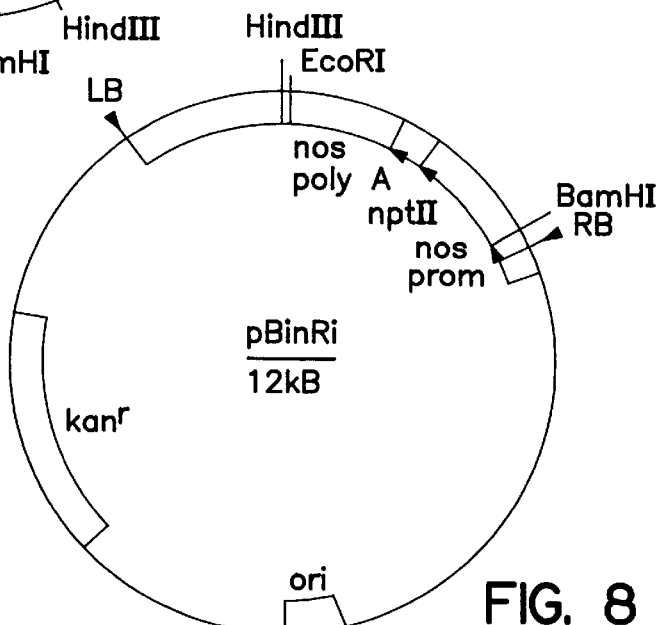
FIG. 8 shows the construction of pBinRi.
Figure 9:
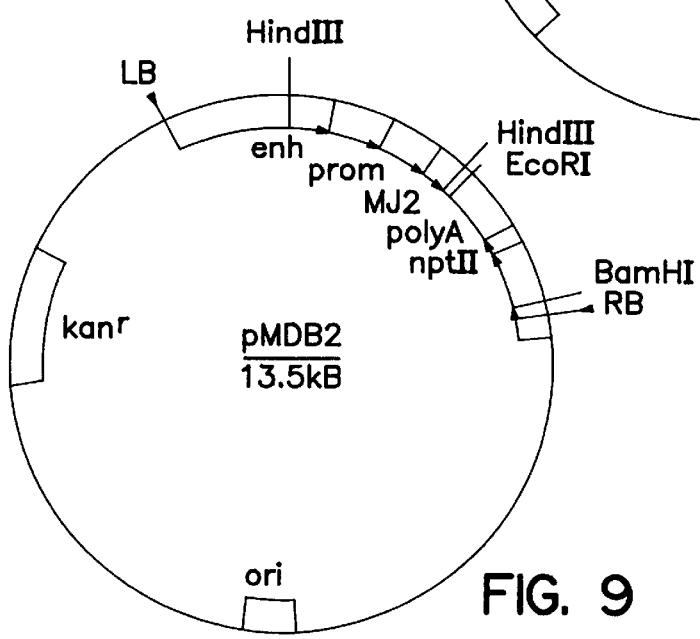
FIG. 9 shows the construction of the plant transformation vector pMDB2.

The MJ2 CaMV35S promoter insert was HindIII digested from pMDB1 and subcloned into the unique HindIII site of pBinRi. pBinRi is a modified version of the plant transformation vector pBin19 (Bevan, 1984, Nucleic Acids Research, 12:22, 8711–8721) wherein the unique EcoR1 and HindIII sites are switched and a wild type npt II gene is included as illustrated in FIG. 8. The new plant transformation vector is designated pMDB2 and is illustrated in FIG. 9.

EXAMPLE 15

Construction of the plant transformation vector pVT2 for vacuolar expression of Mj-AMP2

Figure 10:
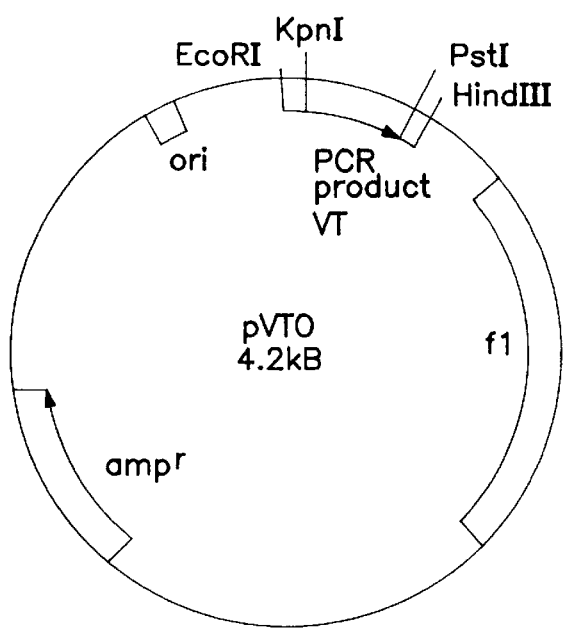
FIG. 10 shows the construction of pVT0.
Figure 11:
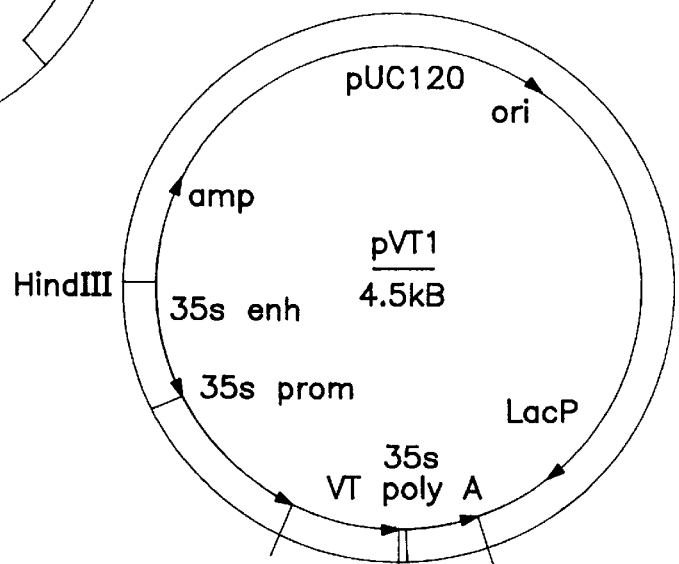
FIG. 11 shows the construction of pVT1.
Figure 12:
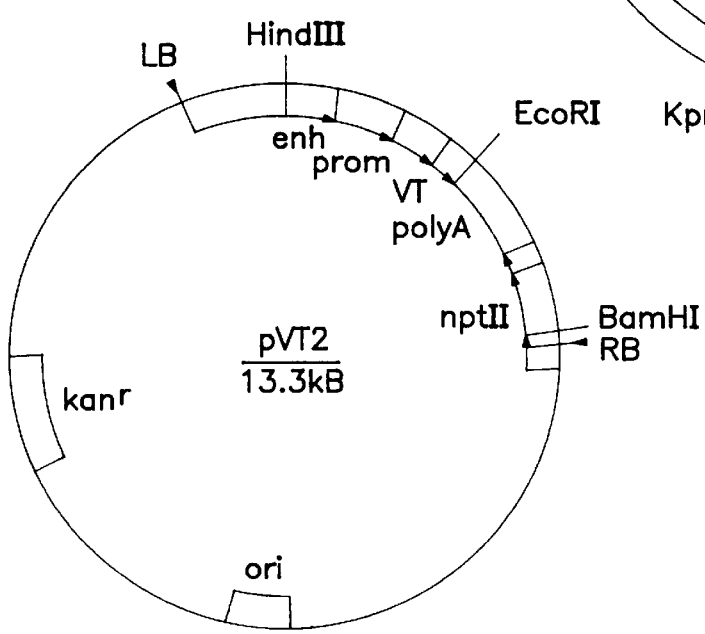
FIG. 12 shows the construction of the plant transformation vector pVT2.

A construct was made to ensure the proper processing and transport of Mj-AMP2 to the vacuoles of transgenic plants. A nucleotide sequence coding for a 15 amino acid propeptide (Bednarek S.Y. et al, 1991, Plant Cell 3, 1195–1206) with an additional amino acid to facilitate cleavage of the propeptide from the mature protein was synthesised. Using PCR techniques, the new synthetic sequence for the propeptide was linked to the plant cDNA encoding the Mj-AMP2 peptide and signal peptide (MJ2) to give the insert designated VT, containing a KpnI site at the 5' end and a PstI site at the 3' end. The KpnI-PstI fragment (generated by PCR) was cloned in the KpnI-PstI site of pEMBL18+ to give pVT0, shown in FIG. 10. The KpnI-PstI fragment of pVT0 was cloned in the KpnI-PstI sites of the plant expression cassette pFF19 to give pVT1, shown in FIG. 11. The HindIII-EcoRI fragment of pVT1 was then cloned in the HindIII-EcoRI site of pBinRi to give the plant transformation vector designated pVT2, shown in FIG. 12.

EXAMPLE 16

Plant Transformation

Agrobacterium strain LBA4404 ACH5 [pAL4404] was transformed to contain either of the vectors pMDB2 or pVT2, using the method of de Framond A et al (Biotechnology, 1, 262–9).

Tobacco transformation was carried out using leaf discs of *Nicotiana tabacum* Samsun based on the method of Hozsch RB et al (1985, Science, 227, 1229–31) and co-culturing with Agrobacterium strains containing pMDB2 or pVT2. Co-cultivation was carried out under selection pressure of 100 µg/ml kanamycin.

Transgenic plants (transformed with pMDB2 or pVT2) were regenerated. These transgenic plants are being analysed for expression of the newly introduced genes using standard Western blotting techniques. Plants capable of constitutive expression of the-introduced genes will be selected and self-pollinated to give seed. F1 seedlings of the transgenic plants will be further analysed.

---

We claim:

1. A transformed biological system comprising a recombinant DNA system coding for an antimicrobial protein selected from the group consisting of the pure protein Mj-AMP1 having SEQ ID NO:1 and the pure protein Mj-AMP2 having SEQ ID NO:2, said system allowing expression of the encoded protein.

2. A biological system as claimed in claim 1 which is a micro-organism.

3. A biological system as claimed in claim 1 which is a plant.

\* \* \* \* \*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 37 amino acids
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: MJ-AMP1 FIGURE 4A (xi) SEQUENCE DESCRIPTION: SEQ ID NO:1:

```
Gln Cys Ile Gly Asn Gly Gly Arg Cys Asn Glu Asn Val Gly Pro Pro
1               5                   10                  15

Tyr Cys Cys Ser Gly Phe Cys Leu Arg Gln Pro Gly Gln Gly Tyr Gly
            20                  25                  30

Tyr Cys Lys Asn Arg
        35
```

(2) INFORMATION FOR SEQ ID NO:2:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: MJ-AMP2 FIGURE 4A (xi) SEQUENCE DESCRIPTION: SEQ ID NO:2:

```
Cys Ile Gly Asn Gly Gly Arg Cys Asn Glu Asn Val Gly Pro Pro Tyr
1               5                   10                  15

Cys Cys Ser Gly Phe Cys Leu Arg Gln Pro Asn Gln Gly Tyr Gly Val
            20                  25                  30

Cys Arg Asn Arg
            35
```

(2) INFORMATION FOR SEQ ID NO:3:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: MJ-AMP1 FIGURE 4B (xi) SEQUENCE DESCRIPTION: SEQ ID NO:3:

```
Gln Cys Ile Gly Asn Gly Gly Arg Cys Asn Glu Asn Val Gly Pro Pro
1               5                   10                  15

Tyr Cys Cys Ser Gly Phe Cys Leu Arg Gln Pro Gly Gln Gly Tyr Gly
            20                  25                  30

Tyr Cys Lys Asn Arg
            35
```

(2) INFORMATION FOR SEQ ID NO:4:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: MJ-AMP2 FIGURE 4B (xi) SEQUENCE DESCRIPTION: SEQ ID NO:4:

```
Cys Ile Gly Asn Gly Gly Arg Cys Asn Glu Asn Val Gly Pro Pro Tyr
1               5                   10                  15

Cys Cys Ser Gly Phe Cys Leu Arg Gln Pro Asn Gln Gly Tyr Gly Val
            20                  25                  30

Cys Arg Asn Arg
            35
```

(2) INFORMATION FOR SEQ ID NO:5:

(i) SEQUENCE CHARACTERISTICS:

(A) LENGTH: 34 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: CONOTOXIN GS FIGURE 4B (xi) SEQUENCE DESCRIPTION: SEQ ID NO:5:

Ala Cys Ser Gly Arg Gly Ser Arg Cys Pro Pro Gln Cys Cys Met Gly
1               5                   10                  15

Leu Arg Cys Gly Arg Gly Asn Pro Gln Lys Cys Ile Gly Ala His Glu
                20                  25                  30

Asp Val (2) INFORMATION FOR SEQ ID NO:6:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: CONOTOXIN MV2A FIGURE 4B (xi) SEQUENCE DESCRIPTION: SEQ ID NO:6:

Cys Lys Gly Lys Gly Ala Ser Cys Arg His Thr Ser Tyr Asp Cys Cys
1               5                   10                  15

Thr Gly Ser Cys Asn Arg Gly Lys Cys
                20                  25

(2) INFORMATION FOR SEQ ID NO:7:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: AGATOXIN 3 FIGURE 4B (xi) SEQUENCE DESCRIPTION: SEQ ID NO:7:

Ala Asp Cys Val Gly Asp Gly Gln Arg Cys Ala Asp Trp Ala Gly Pro
1               5                   10                  15

Tyr Cys Cys Ser Gly Tyr Tyr Cys Ser Cys Arg Ser Met Pro Tyr Cys
                20                  25                  30

Arg Cys Arg Ser Asp Ser
        35

(2) INFORMATION FOR SEQ ID NO:8:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: CURTATOXIN 2 FIGURE 4B (xi) SEQUENCE DESCRIPTION: SEQ ID NO:8:

Ala Asp Cys Val Gly Asp Gly Gln Lys Cys Ala Asp Trp Phe Gly Pro
1               5                   10                  15

Tyr Cys Cys Ser Gly Tyr Tyr Cys Ser Cys Arg Ser Met Pro Tyr Cys
                20                  25                  30

Arg Cys Arg Ser Asp Ser
            35

(2) INFORMATION FOR SEQ ID NO:9:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: BUTHUS PEP 2 FIGURE 4B (xi) SEQUENCE DESCRIPTION: SEQ ID NO:9:

Val Gly Cys Glu Glu Asp Pro Met Asn Cys Lys Gly Lys Gln Ala Lys
1               5                   10                  15

Pro Thr Cys Cys Asn Gly Val Cys Asn Cys Asn Val
                20                  25

(2) INFORMATION FOR SEQ ID NO:10:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: FIGURE 6 AMINO ACID SEQUENCE (xi) SEQUENCE DESCRIPTION: SEQ ID NO:10:

Leu Pro Val Ala Phe Leu Lys Phe Ala Ile Val Leu Ile Leu Phe Ile
1               5                   10                  15

Ala Met Ser Ala Met Ile Glu Ala Gln Cys Ile Gly Asn Gly Gly Arg
                20                  25                  30

Cys Asn Glu Asn Val Gly Pro Pro Tyr Cys Cys Ser Gly Phe Cys Leu
            35                  40                  45

Arg Gln Pro Gly Gln Gly Tyr Gly Tyr Cys Lys Asn Arg
        50                  55                  60

(2) INFORMATION FOR SEQ ID NO:11:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: FIGURE 6 BASE SEQUENCE (xi) SEQUENCE DESCRIPTION: SEQ ID NO:11:

CTTCCCGTTG CCTTCCTCAA ATTCGCTATT GTGTTGATTC TCTTCATTGC CATGTCCGCA    60

```
ATGATAGAAG CACAATGCAT AGGAAATGGA GGAAGATGTA ACGAGAACGT GGGGCCACCA      120

TACTGCTGCT CCGGTTTCTG CCTCCGTCAA CCTGGACAAG GTTATGGATA TTGTAAGAAC      180

CGCTGAGCAA GAGCATGAAA GCAAGGCCAA TGTGTGGTCT ACTAATTTAG CCTCAAATGT      240

TATTTATTTG CATGTCTTGT GTTTCTTAAT TACCTTCTTT GTGTCTAAGA AGGTATAGAT      300

CAATAGTTTC TACTTTACTA CTATGAATAA GAGGCTTTGA TTTGGTTTAA AAAAAAAAAA      360
```

(2) INFORMATION FOR SEQ ID NO:12:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: FIGURE 7 AMINO ACID SEQUENCE MJ-AMP2

(xi) SEQUENCE DESCRIPTION: SEQ ID NO:12:

```
Met Ala Lys Val Pro Ile Ala Phe Leu Lys Phe Val Ile Val Leu Ile
1               5                  10                  15

Leu Phe Ile Ala Met Ser Gly Met Ile Glu Ala Cys Ile Gly Asn Gly
            20                  25                  30

Gly Arg Cys Asn Glu Asn Val Gly Pro Pro Tyr Cys Cys Ser Gly Phe
        35                  40                  45

Cys Leu Arg Gln Pro Asn Gln Gly Tyr Gly Val Cys Arg Asn Arg
    50                  55                  60
```

(2) INFORMATION FOR SEQ ID NO:13:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: FIGURE 7 BASE SEQUENCE MJ-AMP2

(xi) SEQUENCE DESCRIPTION: SEQ ID NO:13:

```
ATATCATTCA AATATACTAA ACTAATTATA AAAAATGGCT AAGGTTCCAA TTGCCTTTCT       60

CAAATTCGTC ATCGTGTTGA TTCTCTTCAT TGCCATGTCA GGCATGATAG AAGCATGCAT      120

AGGAAATGGA GGAAGATGTA ACGAGAACGT GGGCCCACCA TACTGCTGTT CGGGTTTCTG      180

CCTCCGTCAA CCTAACCAAG GTTACGGTGT TTGCAGGAAC CGCTAATAAG CAAAGCCCAA      240

AGTGTGGGTC ACAAAATAGT AGAGTTTAGC CTCAAATGTG GTTTATATAT GTAACAATCT      300

TATATGTGTT TCTCTTGTGT TTCTTAATTA CCTTCTTTGT GTCTAAGAAG GTATGGATAA      360

ATAGTTTGTA CTTTACTATT ATGGTTTTTT CTTATATCAA TAAGAGGCTT TAATTAAAAA      420

AAAAAAAAAA AAA                                                         433
```